United States Patent
LaGrange et al.

(10) Patent No.: US 7,270,684 B2
(45) Date of Patent: Sep. 18, 2007

(54) COMPOSITION FOR DYEING KERATINOUS FIBERS COMPRISING AT LEAST ONE AZODIAZINE DIRECT DYE CONTAINING AN ANILINE GROUP AND DYEING METHOD USING IT

(75) Inventors: Alain LaGrange, Coupvray (FR); Sylvain Kravtchenko, Asnieres (FR)

(73) Assignee: L'Oreal, Paris (FR)

( * ) Notice: Subject to any disclaimer, the term of this patent is extended or adjusted under 35 U.S.C. 154(b) by 30 days.

(21) Appl. No.: 10/902,029

(22) Filed: Jul. 30, 2004

(65) Prior Publication Data

US 2006/0137110 A1    Jun. 29, 2006

Related U.S. Application Data

(60) Provisional application No. 60/510,015, filed on Oct. 10, 2003.

(30) Foreign Application Priority Data

Jul. 30, 2003  (FR) .................................. 03 50388

(51) Int. Cl.
  *A61K 8/00*  (2006.01)
(52) U.S. Cl. .................... 8/405; 8/406; 8/407; 8/409; 8/410; 8/411; 8/412; 8/421; 8/425; 8/657; 8/689; 544/249
(58) Field of Classification Search ............. 8/405, 8/406, 407, 409, 410, 411, 412, 421, 425, 8/657, 689; 544/249
See application file for complete search history.

(56) References Cited

U.S. PATENT DOCUMENTS 2,528,378 A   10/1950  Mannheimer
2,781,354 A    2/1957  Mannheimer
4,395,301 A *  7/1983  Bauer et al. ............. 156/307.5

FOREIGN PATENT DOCUMENTS

| DE | 197 46 137 | 4/1999 |
|---|---|---|
| DE | 203 03 559 | 8/2003 |
| EP | 1 166 754 | 1/2002 |
| FR | 1 285 848 | 4/1961 |

OTHER PUBLICATIONS

STIC Search Report dated Aug. 3, 2006.*
English language Derwent Abstract of DE 197 46 137, Apr. 22, 1999.
English language Derwent Abstract of DE 203 03 559, Aug. 28, 2003.
French Search Report of French Patent Application No. 0350388.
"Handbook of Surfactants", M.R. Porter, Ed. Blackie & Son, Glasgow & London, 1991, 116-178.

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

The present invention relates to a composition for dyeing keratinous fibers, containing at least one azodiazine direct dye corresponding to the following formula (I):

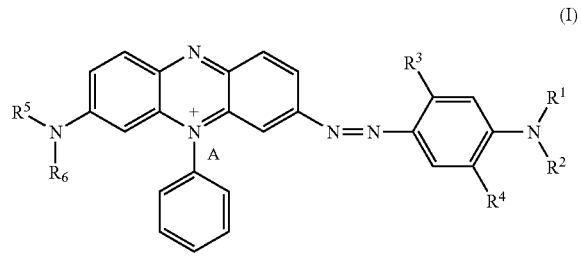

The present invention also relates to a method for dyeing keratinous fibers using these direct dyes.

31 Claims, No Drawings

COMPOSITION FOR DYEING KERATINOUS FIBERS COMPRISING AT LEAST ONE AZODIAZINE DIRECT DYE CONTAINING AN ANILINE GROUP AND DYEING METHOD USING IT

This application claims the benefit of U.S. Provisional Application No. 60/510,015, filed Oct. 10, 2003, which is herein incorporated by reference.

The present disclosure relates to compositions for dyeing keratinous fibers, such as human keratinous fibers, for example, hair, comprising at least one direct dye belonging to the azodiazine compound family. The disclosure also relates to the use of certain compounds of the azodiazine family as direct dyes in compositions for dyeing keratinous fibers. The present disclosure also relates to methods for dyeing keratinous fibers using such compositions.

The use of dyeing compositions containing oxidation dye precursors (such as ortho- or para-phenylenediamines, ortho- or para-aminophenols, generally called "oxidation bases") and optionally couplers (meta-phenylenediamines, meta-aminophenols and meta-diphenols also called color modifiers) is known in the art to dye keratinous fibers such as hair. Oxidation dye precursors are colorless or faintly colored precursors which, when combined with oxidizing products (such as hydrogen peroxide) give rise, through an oxidation process, to colored and dyeing compounds.

However, the current methods for oxidation dyeing may have the following disadvantages:

they can cause degradation of the keratinous fibers and a bothersome irritation of the scalp because of the use of oxidizing products such as hydrogen peroxide;

they generate a fast color of the keratinous fibers, which may change over time; and they often cause selectivity in fiber color, i.e., differences in color along the same fiber.

To avoid the abovementioned disadvantages, it has been proposed to use direct dyes, which dye the hair by causing a colored molecule (the direct dye) to penetrate, by diffusion, into the hair without using hydrogen peroxide.

However, direct dyeing methods have proved, up until now, unsatisfactory for reasons that including the following:

they cause insufficient color fastness, i.e., the color fades after shampooing a few times; and they also cause selectivity in the color of the fibers, i.e., differences in color along the same keratinous fiber.

A need therefore still exists for compositions for dyeing keratinous fibers, which are not very selective, can give a large variety of and intense colors and can give a fast fiber color which changes little over time.

Thus, the present inventors have found that certain azodiazine compounds incorporated in compositions for dyeing keratinous fibers make it possible to overcome at least one of the disadvantages encountered in the prior art and make it possible to obtain a range of highly varied colors, a very low selectivity, and/or also a good level of fastness.

Accordingly, in one aspect, the disclosure provides compositions for dyeing keratinous fibers comprising at least one dye chosen from the compounds of formula (I):

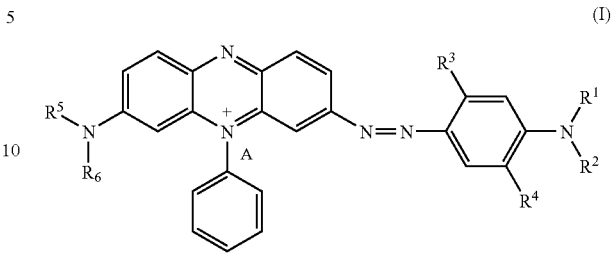

(I)

wherein:

$R^1$ and $R^2$, independently of each other, are chosen from:
  a hydrogen atom; and
  alkyl groups having from 1 to 30 carbon atoms, for example, from 1 to 4 carbon atoms, and which are optionally substituted with one or more hydroxy groups;

$R^3$ is chosen from a hydrogen atom, alkyl groups having from 1 to 30 carbon atoms, for example, from 1 to 4 carbon atoms, and hydroxy groups;

$R^4$ is chosen from a hydrogen atom or alkyl groups having from 1 to 30 carbon atoms, for example, from 1 to 4 carbon atoms;

$R^5$ and $R^6$ comprise, independently of each other, alkyl groups having from 1 to 30 carbon atoms, for example, from 1 to 4 carbon atoms, or together with the nitrogen atom to which they are attached form a heterocycle; and A comprises an anionic counterion.

As used herein, the term "alkyl group" means a linear or branched alkyl group having from 1 to 30 carbon atoms, for example, methyl, ethyl, n-propyl, i-propyl, n-butyl, i-butyl, and t-butyl groups.

As used herein, the term "counterion" means any anion capable of neutralizing the positive charge carried by the positively charged nitrogen atom of the tricyclic unit of the compounds of formula (I). This counterion may be a halide (such as a chloride, bromide, iodide), a sulphate, a methosulphate, a phosphate, or a tosylate.

The compounds of formula (I) may be direct dyes, i.e., they do not require developing with another agent such as an oxidation dye.

According to one embodiment, the compounds of formula (I) are provided wherein when $R^1$ and $R^2$ comprise a methyl group and $R^5$ and $R^6$ comprise an ethyl group, $R^3$ and $R^4$ are different from a hydrogen atom.

In certain embodiments, the at least one direct dye described herein is chosen from compounds of formulae (II) and (III):

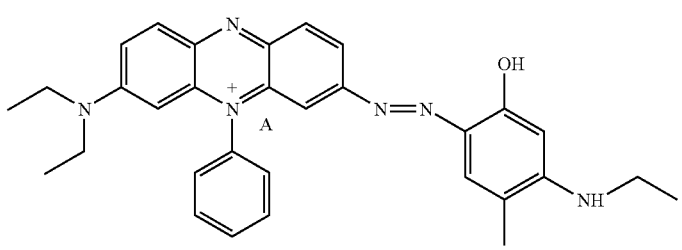

(II)

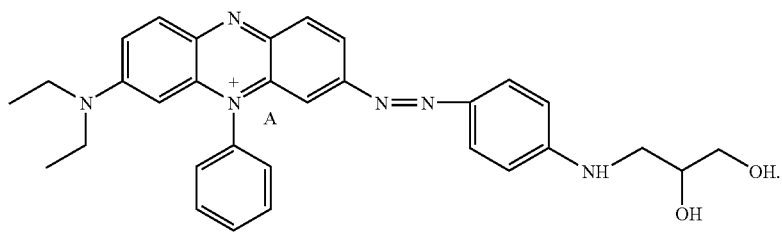

(III)

In some of these embodiments, A is a chloride ion.

One such dye of formula (II) is Basic Dye Copying Black SK, STK (CAS 6408-43-1).

One such dye of formula (III) is Basic Dye Copying Black 1059, L527 (CAS 6441-65-2).

The dye compositions described herein make it possible to obtain intense colors on natural and on sensitized hair.

These dye compositions also make it possible to obtain varying glints which are chromatic or dark, very intense, not very selective, and exhibit good fastness.

Additionally, the dye compositions make it possible to obtain neutral gray and black glints which change little over time.

The content of the dye or dyes chosen from compounds of formula (I) can vary between approximately 0.001 and 20%, for example, 0.01 and 10% or even 0.1 and 5%, by weight relative to the total weight of the dyeing composition.

The dyeing compositions may optionally comprise an aqueous medium comprising water or a mixture of water and a cosmetically acceptable organic solvent. Examples of cosmetically acceptable organic solvents include, but are not limited to, alcohols such as ethyl alcohol, isopropyl alcohol, benzyl alcohol, polyols, polyol ethers; alkanes; ketones; and mixtures thereof.

In addition, the compositions may comprise one or more direct dye different from the compounds of formula (I). These direct dyes may be chosen from any dyes known in the art to be used in direct dyeing. The additional direct dye or dyes may be nonionic, cationic, or amphoteric, and include, but are not limited to, commonly used aromatic and/or nonaromatic dyes such as nitro dyes, methines, azomethines, styriles, triarylmethanes, diarylmethanes, azo dyes, anthraquinone and naphthoquinone dyes, porphyrins, tetraphenylporphyrins, metalloporphyrins, phthalocyanines, natural dyes of the carotenoid, terpenoid and flavonoid type, and fluorescent dyes such as fluorescein, rhodamine, and coumarin.

The composition disclosed herein may additionally comprise at least one oxidation base optionally combined with at least one coupler conventionally used for oxidation dyeing.

By way of example, oxidation bases, include, but are not limited to, para-phenylenediamines, bisphenylalkylenediamines, para-aminophenols, ortho-aminophenols, and heterocyclic bases such as diaminopyrazoles.

The couplers may, for example, comprise meta-phenylenediamine couplers, meta-aminophenol couplers, meta-diphenol couplers, naphthalenic couplers, or heterocyclic couplers.

The compositions may also further comprise one or more customary additives for dyeing compositions, for example, surfactants, thickening agents, antioxidants, sequestering agents, dispersing agents, hair conditioners, preservatives, opacifying agents, acidifying agents, basifying agents, and perfumes.

It is understood that persons skilled in the art can make an appropriate choice of these additives such that the properties of the compositions which are inherent to the presence of the compounds of formula (I) as defined above are not impaired by the abovementioned additives with no more than routine skill. The surfactant or surfactants may be chosen from anionic, nonionic, amphoteric or cationic surfactants. Suitable, anionic, nonionic, amphoteric or cationic surfactants include, but are not limited to:

Anionic Surfactants:

Anionic surfactants which may be used, alone or as mixtures, include salts, such as alkali metal salts (e.g., sodium salts, magnesium salts, ammonium salts, amine salts, amino alcohol salts, and the like) of the following compounds: alkyl sulfates, alkyl ether sulfates, alkyl amidoether sulfates, alkyl aryl polyether sulfates, monoglyceride sulfates; alkyl sulfonates, alkyl phosphates, alkyl amide sulfonates, alkyl aryl sulfonates, α-olefin sulfonates, paraffin sulfonates; ($C_6$-$C_{24}$)alkyl sulfosuccinates, ($C_6$-$C_{24}$)alkyl ether sulfosuccinates, ($C_6$-$C_{24}$)alkyl amide sulfosuccinates, ($C_6$-$C_{24}$)alkyl sulfoacetates; ($C_6$-$C_{24}$)acyl sarcosinates, and ($C_6$-$C_{24}$)acyl glutamates.

Additional anionic surfactants include ($C_6$-$C_{24}$)alkyl polyglycoside carboxylic esters such as alkyl polyglucoside citrates, alkyl polyglucoside tartrates, alkyl polyglucoside sulfosuccinates, and alkyl polyglucoside sulfosuccinamates; acyl isethionates and N-acyltaurates, the alkyl or acyl radical of all these compounds which may have from 12 to 20 carbon atoms, and wherein the aryl radical may comprise a phenyl or benzyl group.

Anionic surfactants also include salts of fatty acids such as the salts of oleic, ricinoleic, palmitic and stearic acids; acids of copra oil or of hydrogenated copra oil; acyl lactylates whose acyl radical contains from 8 to 20 carbon atoms; alkyl D-galactoside uronic acids and salts thereof; polyoxyalkylenated ($C_6$-$C_{24}$)alkyl ether carboxylic acids, polyoxyalkylenated ($C_6$-$C_{24}$)alkyl amidoether carboxylic acids and salts thereof, such as those containing from 2 to 50 alkylene oxide groups, e.g., ethylene oxide groups; and mixtures thereof.

Nonionic Surfactants:

Useful nonionic surfactants are compounds which are well known per se and are described, for example, in the "Handbook of Surfactants", M. R. PORTER, Ed. Blackie & Son, Glasgow and London, 1991, 116-178.

Nonionic surfactants may be used alone or as mixtures, and include, but are not limited to, alcohols, α-diols, polyethoxylated and polypropoxylated alkylphenols having a fatty chain containing, for example, from 8 to 18 carbon atoms or wherein the number of ethylene oxide or propylene oxide groups ranges from 2 to 50; copolymers of ethylene oxide and propylene oxide; condensates of ethylene oxide and propylene oxide with fatty alcohols; polyethoxylated fatty amides, such as those having from 2 to 30 mol of ethylene oxide; polyglycerolated fatty amides containing on average from 1 to 5, for example, from 1.5 to 4, glycerol groups; oxyethylenated fatty acid esters of sorbitan containing from 2 to 30 mol of ethylene oxide; fatty acid esters of sucrose; fatty acid esters of polyethylene glycol; alkyl polyglycosides; derivatives of N-alkyl glucamine; and amine oxides such as ($C_{10}$-$C_{14}$)alkyl amine oxides and N-acylaminopropylmorpholine oxides.

Amphoteric Surfactants:

The amphoteric (or zwitterionic) surfactants may be used alone or as mixtures, and include but are not limited to, derivatives of aliphatic secondary or tertiary amines with aliphatic radicals which are a linear or branched chain comprising from 8 to 18 carbon atoms and also comprising at least one water-solubilizing anionic group, for example, a carboxylate, a sulfonate, a sulphate, a phosphate, or a phosphonate.

Amphoteric surfactants also include ($C_8$-$C_{20}$)alkyl betaines, sulfobetaines, ($C_8$-$C_{20}$)alkyl amido($C_1$-$C_6$)alkyl betaines, and ($C_8$-$C_{20}$)alkyl amido($C_1$-$C_6$)alkyl sulfobetaines.

Among the amine derivatives, there may be mentioned the compounds marketed by the company Rhodia Chimie under the trade name Miranol®, which are described in U.S. Pat. Nos. 2,528,378 and 2,781,354 and which are classified in the CTFA Dictionary, $5^{th}$ edition, 1993, under the names "disodium cocoamphodiacetate", "disodium lauroamphodiacetate", "disodium caprylamphodiacetate", "disodium caprylamphodiacetate", "disodium cocoamphodipropionate", "disodium lauroamphodipropionate", "disodium caprylamphodipropionate", "disodium capryloamphodipropionate", "lauroamphodiproponic acid" and "cocoamphodipropionic acid".

Cationic Surfactants:

Cationic surfactants which may be used alone or as mixtures, include, but are not limited to, salts of optionally polyoxyalkylenated primary, secondary and tertiary fatty amines; quaternary ammonium salts such as tetraalkylammonium, alkylamidoalkyltrialkylammonium, trialkylbenzylammonium, trialkylhydroxyalkylammonium and alkylpyridinium chlorides and bromides; imidazoline derivatives; and cationic amine oxides.

The thickening agents which may used in the compositions may be inorganic or organic and include, but are not limited to, thickening polymers of natural origin such as gums (such as xanthan gum, carob gum, and guar gum), and thickening polymers of synthetic origin (such as hydroxyethylcellulose and polyacrylic acids). The synthetic polymers include associative polymers comprising a fatty chain, such as associative polymers of the acrylic or polyurethane type.

The pH of the dyeing composition generally ranges from 3 to 12, such as from 5 to 11, and such as from 6 to 10.

This pH may be adjusted to the desired value by addition of acidifying or alkalinizing agents generally used in dyeing keratinous fibers or alternatively with the aid of conventional buffer systems to the composition.

Acidifying agents, include, but are not limited to, inorganic or organic acids such as hydrochloric acid, orthophosphoric acid, sulfuric acid, carboxylic acids such as acetic acid, tartaric acid, citric acid, lactic acid, and sulfonic acids.

Alkalinizing agents include, but are not limited to, aqueous ammonia, alkali metal carbonates, alkanolamines such as mono-, di- and triethanolamines and derivatives thereof, sodium or potassium hydroxides and compounds of formula (IV):

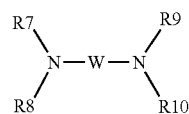

(IV)

wherein W is a propylene residue optionally substituted with a hydroxyl group or a $C_1$-$C_4$ alkyl radical; $R_7$, $R_8$, $R_9$, and $R_{10}$, which are identical or different, each are chosen from a hydrogen atom, a $C_1$-$C_4$ alkyl, and a $C_1$-$C_4$ hydroxyalkyl radical.

The cosmetic compositions may be provided in various galenic forms such as a lotion, a cream, a gel or any other appropriate form for dyeing keratinous fibers. They may also be packaged under pressure in an aerosol can in the presence of a propellant, for example, to form a mousse.

The disclosure also relates to the use of compounds of formula (I) as direct dyes in compositions as described above for dyeing keratinous fibers, including human keratinous fibers, such as the hair.

The disclosure also provides methods for the direct dyeing of keratinous fibers, comprising:

(a) applying to the keratinous fibers a dyeing composition as defined above;

(b) leaving the composition on the keratinous fibers for a sufficient leave-in time to obtain a color;

(c) optionally rinsing the keratinous fibers so as to remove the dyeing composition therefrom;

(d) optionally washing the keratinous fibers once or several times, rinsing them after each wash; and (e) drying the keratinous fibers.

The method may be performed successively as written above.

Thus, the direct dyeing method comprises applying to the hair to be dyed the dyeing composition as defined above, and then leaving in, generally for a leave-in time of 3 to 60 minutes, e.g., of 5 to 40 minutes, such as 15 to 30 minutes, so as to give the composition time to properly act on the hair. This leave-in phase may be carried out at a temperature ranging from room temperature to 80° C., such as from 25 to 55° C.

Next, the keratinous fibers thus dyed are optionally rinsed in order to remove the dyeing composition which has reacted with the fibers and optionally washed once or several times.

When the dyeing composition contains at least one compound of formula (I) and at least one oxidation dye, as mentioned above, the dyeing method requires an additional step for developing, with an oxidizing agent, the color of the oxidation dye.

Consequently, the disclosure also relates to a method for dyeing keratinous fibers comprising:

(f) applying to the keratinous fibers a dyeing composition comprising at least one compound of formula (I) as defined above and at least one oxidation dye, the color of the oxidation dye being developed with an oxidizing agent;

(g) leaving the composition on the keratinous fibers for a sufficient leave-in time to obtain a desired color;

(h) optionally rinsing the keratinous fibers in order to remove the dyeing composition therefrom;

(i) optionally washing the keratinous fibers once or several times, rinsing them after each wash; and (j) drying the keratinous fibers.

The oxidizing agents which may be used are chosen, for example, from hydrogen peroxide, urea peroxide, alkali metal bromates, persalts such as perborates and persulphates, peracids and oxidase enzymes such as peroxidases, oxidoreductases containing two electrons such as uricases, and oxygenases containing four electrons such as laccases. In one embodiment, the oxidizing agent is hydrogen peroxide.

The at least one oxidizing agent may be added to the composition just at the time of use or it may be used from an oxidizing composition containing it.

The compositions are left in, generally for 3 to 60 minutes, such as for 5 to 40 minutes or for 15 to 30 minutes, so as to give the composition enough time to properly act on the hair and for development to take place. This leave-in phase may be carried out at a temperature ranging from room temperature (25° C.) to 80° C., such as from 25 to 55° C.

The invention is illustrated in greater detail by the examples described below. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

EXAMPLE 1

A dyeing composition 1 having the ingredients described in Table 1 below was prepared. This composition comprises a dye (1) (molecular weight: 540 g/mol) in accordance with the disclosure, corresponding to the following formula:

TABLE 1

| Ingredients | Quantity |
|---|---|
| Dye (1) | 0.54 g |
| Benzyl alcohol | 4 g |
| Polyethylene glycol 6 EO | 6 g |
| Hydroxyethylcellulose | 0.7 g |
| Alkyl polyglucoside as an aqueous solution containing 60% AM* | 4.5 g AM* |
| Phosphate buffer | qs pH 7 |
| Demineralized water | qs 100 g |

*AM: Active material.

EXAMPLE 2

A dyeing composition 2 having the ingredients described in Table 2 below was prepared. This composition comprises a dye (2) (molecular weight: 556 g/mol) in accordance with the disclosure, corresponding to the following formula:

TABLE 2

| Ingredients | Quantity |
|---|---|
| Dye (2) | 0.55 g |
| Benzyl alcohol | 4 g |
| Polyethylene glycol 6 EO | 6 g |

TABLE 2-continued

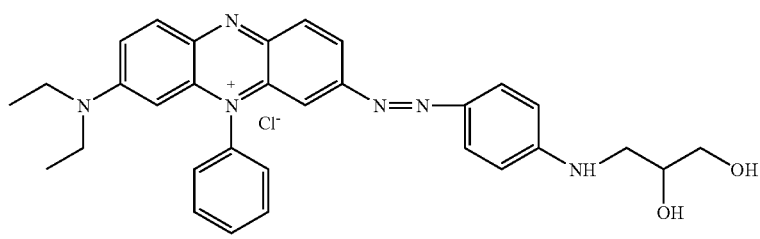

| Ingredients | Quantity |
| --- | --- |
| Hydroxyethylcellulose | 0.7 g |
| Alkyl polyglucoside as an aqueous solution containing 60% AM* | 4.5 g AM* |
| Phosphate buffer | qs pH 7 |
| Demineralized water | qs 100 g |

*AM: Active material.

What is claimed is:

1. A composition for dyeing keratinous fibers comprising at least one direct dye chosen from compounds of formula (I):

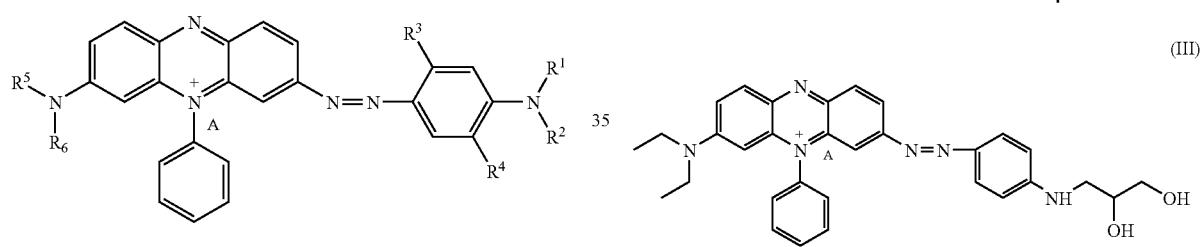

wherein:
- $R^1$ and $R^2$ are, independently of each other, chosen from:
  - a hydrogen atom; and
  - alkyl groups having from 1 to 30 carbon atoms, said alkyl groups optionally substituted with one or more hydroxy groups;
- $R^3$ is chosen from a hydrogen atom, alkyl groups having from 1 to 30 carbon atoms, and hydroxy groups;
- $R^4$ is chosen from a hydrogen atom and alkyl groups having from 1 to 30 carbon atoms;
- $R^5$ and $R^6$, independently of each other, comprise alkyl groups having from 1 to 30 carbon atoms, or together with the nitrogen atom to which they are attached form a heterocycle; and
- A comprises an anionic counterion;

wherein said at least one direct dye is present in an amount sufficient to dye keratinous fibers.

2. The composition according to claim 1, wherein the at least one direct dye is chosen from compounds of formulae (II) and (III):

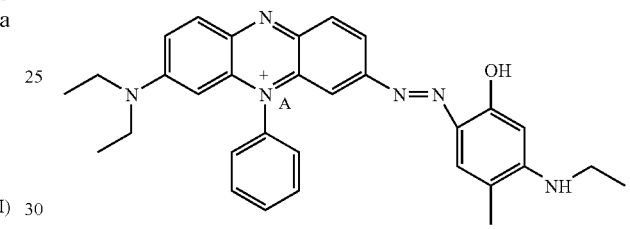

wherein A comprises an anionic counterion.

3. The composition according to claim 1, wherein the at least one direct dye is present in the composition in an amount ranging from 0.001 to 20% by weight of the total weight of the composition.

4. The composition according to claim 3, wherein the at least one direct dye is present in the composition in an amount ranging from 0.01 to 10% by weight of the total weight of the composition.

5. The composition according to claim 4, wherein the at least one direct dye is present in the composition in an amount ranging from 0.1 to 5% by weight of the total weight of the composition.

6. The composition according to claim 1, further comprising an aqueous medium comprising water or a mixture of water and a cosmetically acceptable organic solvent.

7. The composition according to claim 6, wherein the cosmetically acceptable organic solvent is chosen from alcohols, alkanes, ketones, and mixtures thereof.

8. The composition according to claim 7, wherein the alcohols are chosen from ethyl alcohol, isopropyl alcohol, benzyl alcohol, polyols, and polyol ethers.

9. The composition according to claim 1, further comprising at least one additional direct dye different from the at least one direct dye chosen from compounds of formula (I).

10. The composition according to claim 9, wherein the at least one additional direct dye is chosen from nitro dyes, methines, azomethines, styriles, triarylmethanes, diarylmethanes, azo dyes, anthraquinone dyes, naphthoquinone dyes, porphyrins, tetraphenylporphyrins, metalloporphyrins, phthalocyanines, natural carotenoid dyes, natural terpenoid dyes, natural flavonoid dyes, and fluorescent dyes.

11. The composition according to claim 10, wherein the fluorescent dyes are chosen from fluorescein, rhodamine, and coumarin.

12. The composition according to claim 1, further comprising at least one oxidation base optionally combined with at least one coupler.

13. The composition according to claim 12, wherein the at least one oxidation base is chosen from para-phenylenediamines, bisphenylalkylenediamines, para-aminophenols, ortho-aminophenols, and heterocyclic bases.

14. The composition according to claim 12, wherein the at least one coupler is chosen from meta-phenylenediamine couplers, meta-aminophenol couplers, meta-diphenol couplers, naphthalenic couplers, and heterocyclic couplers.

15. The composition according to claim 1, further comprising at least one additive chosen from surfactants, thickening agents, antioxidants, sequestering agents, dispersing agents, hair conditioners, preservatives, opacifying agents, acidifying agents, basifying agents, and perfumes.

16. The composition according to claim 1, having a pH ranging from 3 to 12.

17. The composition according to claim 16, said pH ranging from 5 to 11.

18. The composition according to claim 17, said pH ranging from 6 to 10.

19. A method for the direct dyeing of keratinous fibers, comprising:
applying to the keratinous fibers at least one direct dye chosen from compounds of formula (I):

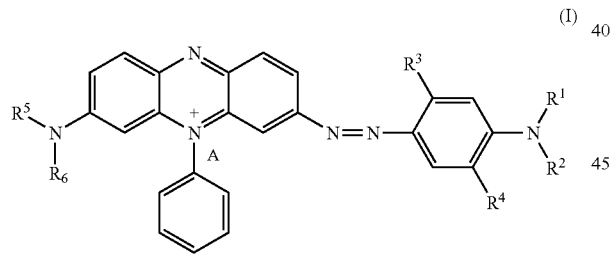

wherein:
R$^1$ and R$^2$ are, independently of each other, chosen from:
a hydrogen atom; and
alkyl groups having from 1 to 30 carbon atoms, said alkyl groups optionally substituted with one or more hydroxy groups;
R$^3$ is chosen from a hydrogen atom, alkyl groups having from 1 to 30 carbon atoms, and hydroxy groups;
R$^4$ is chosen from a hydrogen atom and alkyl groups having from 1 to 30 carbon atoms;
R$^5$ and R$^6$, independently of each other, comprise alkyl groups having from 1 to 30 carbon atoms, or together with the nitrogen atom to which they are attached form a heterocycle; and
A comprises an anionic counterion;
leaving the composition on the keratinous fibers for a sufficient time to obtain a color;
optionally rinsing the keratinous fibers to remove the dyeing composition;
optionally washing the keratinous fibers one or more times, rinsing after each wash; and
drying the keratinous fibers.

20. The method according to claim 19, wherein the composition is left on the keratinous fibers for a time ranging from 3 to 60 minutes.

21. The method according to claim 20, wherein the composition is left on the keratinous fibers for a time ranging from 5 to 40 minutes.

22. The method according to claim 21, wherein the composition is left on the keratinous fibers for a time ranging from 15 to 30 minutes.

23. A method for dyeing keratinous fibers comprising:
applying to the keratinous fibers (a) at least one oxidation dye having a first color developed with an oxidizing agent and (b) at least one direct dye chosen from compounds of formula (I):

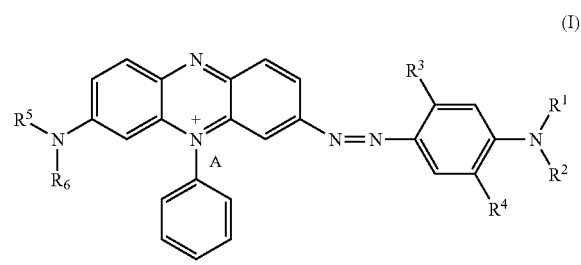

wherein:
R$^1$ and R$^2$ are, independently of each other, chosen from:
a hydrogen atom; and
alkyl groups having from 1 to 30 carbon atoms, said alkyl groups optionally substituted with one or more hydroxy groups;
R$^3$ is chosen from a hydrogen atom, alkyl groups having from 1 to 30 carbon atoms, and hydroxy groups;
R$^4$ is chosen from a hydrogen atom and alkyl groups having from 1 to 30 carbon atoms;
R$^5$ and R$^6$ are, independently of each other, comprise alkyl groups having from 1 to 30 carbon atoms, or together with the nitrogen atom to which they are attached form a heterocycle; and
A comprises an anionic counterion;
leaving the composition on the keratinous fibers for a sufficient time to obtain a second color on the keratinous fibers;
optionally rinsing the keratinous fibers to remove the dyeing composition;
optionally washing the keratinous fibers one or more times, rinsing them after each wash; and
drying the keratinous fibers.

24. The method according to claim 23, wherein the composition is left on the keratinous fibers for a time ranging from 3 to 60 minutes.

25. The method according to claim 24, wherein the composition is left on the keratinous fibers for a time ranging from 5 to 40 minutes.

26. The method according to claim 25, wherein the composition is left on the keratinous fibers for a time ranging from 15 to 30 minutes.

27. The method according to claim 23, wherein the oxidizing agent is chosen from hydrogen peroxide, urea peroxide, alkali metal bromates, persalts, peracids, and oxidase enzymes.

28. The method according to claim 27, wherein the persalts are chosen from perborates and persulphates.

29. The method according to claim 27, wherein the oxidase enzymes are chosen from peroxidases, oxidoreductases containing two electrons, and oxygenases containing four electrons.

30. The method according to claim 29, wherein the oxidoreductase containing two electrons comprise a uricase.

31. The method according to claim 29, wherein the oxygenase containing four electrons comprises a laccase.

* * * * *

UNITED STATES PATENT AND TRADEMARK OFFICE
CERTIFICATE OF CORRECTION

PATENT NO. : 7,270,684 B2  Page 1 of 1
APPLICATION NO. : 10/902029
DATED : September 18, 2007
INVENTOR(S) : Alain Lagrange et al.

It is certified that error appears in the above-identified patent and that said Letters Patent is hereby corrected as shown below:

In claim 23, column 12, line 47, "$R^5$ and $R^6$ are," should read --$R^5$ and $R^6$,--.

In claim 30, column 14, line 6, "oxidoreductase" should read --oxidoreductases--.

In claim 31, column 14, line 8, "oxygenase" should read --oxygenases--.

In claim 31, column 14, line 8, "comprises" should read --comprise--.

Signed and Sealed this

Twenty-fifth Day of December, 2007

JON W. DUDAS
*Director of the United States Patent and Trademark Office*